(12) United States Patent
Zambelli

(10) Patent No.: US 9,084,833 B2
(45) Date of Patent: Jul. 21, 2015

(54) METHOD FOR SANIFYING/STERILIZING CORK STOPPERS

(75) Inventor: Floriano Zambelli, Rovereto (IT)

(73) Assignee: BRENTAPACK S.R.L., Borgo Valsugana (Trento) (IT)

( * ) Notice: Subject to any disclaimer, the term of this patent is extended or adjusted under 35 U.S.C. 154(b) by 9 days.

(21) Appl. No.: 13/995,744

(22) PCT Filed: Jul. 30, 2012

(86) PCT No.: PCT/EP2012/003229
§ 371 (c)(1),
(2), (4) Date: Jun. 19, 2013

(87) PCT Pub. No.: WO2013/017250
PCT Pub. Date: Feb. 7, 2013

(65) Prior Publication Data
US 2013/0270213 A1 Oct. 17, 2013

(30) Foreign Application Priority Data

Aug. 3, 2011 (IT) ................ VI2011A0222

(51) Int. Cl.
*A61L 2/18* (2006.01)
*A61L 2/232* (2006.01)
*A61L 2/235* (2006.01)
*B67B 1/03* (2006.01)
*C23C 14/02* (2006.01)
*C23C 14/06* (2006.01)
*C23C 14/22* (2006.01)
*B65D 39/00* (2006.01)
*B05D 7/08* (2006.01)
*B05D 1/00* (2006.01)
*B27K 7/00* (2006.01)
*B82Y 99/00* (2011.01)

(52) U.S. Cl.
CPC . *A61L 2/18* (2013.01); *A61L 2/232* (2013.01); *A61L 2/235* (2013.01); *B05D 1/62* (2013.01); *B05D 7/08* (2013.01); *B65D 39/0011* (2013.01); *B67B 1/03* (2013.01); *C23C 14/021* (2013.01); *C23C 14/0605* (2013.01); *C23C 14/228* (2013.01); *A61L 2202/17* (2013.01); *B27K 7/00* (2013.01); *B82Y 99/00* (2013.01)

(58) Field of Classification Search
CPC ......................................................... A61L 2/18
USPC .............................. 422/28; 977/773; 215/355
See application file for complete search history.

(56) References Cited

FOREIGN PATENT DOCUMENTS

| | | |
|---|---|---|
| EP | 1 826 248 A1 | 8/2007 |
| IT | 1 048 882 B | 12/1980 |

OTHER PUBLICATIONS

International Search Report and Written Opinion of the International Searching Authority in PCT/EP2012/003229 mailed Dec. 7, 2012.
Robertson: "Diamond-like amorphous carbon," Materials Science and Engineering R, 37, 2002, pp. 129-281.

*Primary Examiner* — Sean E Conley
(74) *Attorney, Agent, or Firm* — Collard & Roe, P.C.

(57) ABSTRACT

There is provided a method for sanifying/sterilizing cork stoppers, from the least expensive provided with an agglomerated body and washers to the finest made of high quality natural cork, used in bottle capping, and the cork stoppers thereby produced. The method includes applying a film having a reticulated structure with cells smaller than the cork cells of the stopper on the surface of the cork cells and on the outer surface of the stopper.

4 Claims, No Drawings

METHOD FOR SANIFYING/STERILIZING CORK STOPPERS

CROSS REFERENCE TO RELATED APPLICATIONS

This application is the National Stage of PCT/EP2012/003229 filed on Jul. 30, 2012, which claims priority under 35 U.S.C. §119 of Italian Application No. VI2011A000222 filed on Aug. 3, 2011, the disclosure of which is incorporated herein by reference. The international application under PCT article 21(2) was published in English.

The present finding relates to a method for sanifying/sterilizing cork stoppers, from the cheapest ones, provided with an agglomerated body and washers, to the finest ones made of high quality natural cork, used in bottle capping.

As is well known by the people in charge of the field of bottle capping and by single consumers, caps are a decisive element for ensuring perfect storage of the bottled product.

To prevent the bottled wine from being contaminated by the well-known "cork stopper odour", the cork stopper is subject to a sanification/sterilization treatment which is intended for eliminating the polluting substances contained in the cork mass and which cause organoleptic problems to the wine.

According to the prior art, several methods for sanifying/sterilizing cork stoppers are known, ranging from the washing in hot water to the use of UHV rays (gamma 25 kGy rays).

While such methods achieve the object of neutralising the polluting action of the stopper, they exhibit the drawback of affecting the cork mass, thus altering the physical-chemical features of the stopper.

The most important prior art documents are: EP 1 826 248 A1 and IT 1 048 882 B.

The object of the present finding is to provide a sanification/sterilization method to subject the cork stoppers to make them "neutral" relative to the bottled contents, without altering the chemical-physical properties of the cork.

Such object is achieved by providing a method characterised by applying a film on the outer surface of the cork cells of the stopper which, in addition to not affecting the organic components found in the cork, allows the mass to "transpire" and thereby to be TCA (trichloroanisole)-proof, a substance which gives to the wine the typical "cork stopper odour", and TeCA (tetrachloroanisole)-proof, which causes the as typical "mould taste".

In particular, the method of the finding provides for coating the surface of cork cells of the stopper with a film having a morphologically reticulated structure with cells being smaller in size than the cork cells and such as to allow the passage of oxygen; at the same time, such film acts as a barrier against dust and impurities that may penetrate the cork mass to pollute it.

Such method is made possible by recent studies on the so-called "nanotechnologies", which have allowed thin membranes to be made, known as "nanostructures".

In the practice the cork stopper, the cells whereof have a reticulated structure having the size in the order of $10^{-3}$, is permeated with material that adheres to the cork cells, forming a film having a nanometric grain size, i.e. in the order of $10^{-9}$.

Studies, laboratory tests and scientific articles (by way of an example we may mention Robertson J. (2002) "Diamond-like Amorphous Carbon", Material Scienze and Engineering R: Reports, 37 (4-6), pages 129-281. ISSN 0927-796X) have confirmed that among the various types of films for coating the products, known as "nanostructured coating", the most suitable ones (also because they are biocompatible) are those derived from Carbon, from Carbon derivatives, such as acetylene ($C_2H_2$) or from other amorphous Carbon structures, in particular Adamantane ($C_{10}H_{16}$).

Operatively, the method of the finding is divided into two operations.

The first operation, called "surface sanification and preparation", consists in "cleaning" the cork through two steps:
  a material cleaning step, which is carried out within vacuum apparatuses ($10^{-2}$ to $10^{-8}$ bar) and at low temperature (max 60° C.), having the function of releasing gases from the cork mass.
  a washing step, introducing into the vacuum apparatus ($10^{-2}$ to $10^{-8}$ bar) gases such as H, helium, nitrogen, argon or mixtures of such gases, which have the function of eliminating and/or inhibiting the organic material inside and on the surface of the stopper.

The second operation, called "nanomaterial deposit", consists in coating the stopper and the cork cell surface with the nanostructured film.

In the practice, nanomaterials are deposited through "vacuum" techniques, such as PVD (Plasma Vapour Deposition), in particular the carbon compounds mentioned above, into the interstices between the cork cells forming the stopper in order to coat them with a nanomaterial film.

It is also noted that in the practice, the coating with a nanostructured film has proved to be convenient also on synthetic material caps, in the different types of mixtures.

The invention claimed is:

1. A method for sanifying/sterilizing cork stoppers used in bottle capping, said method comprising coating the surfaces of the cork cells of the cork stoppers and the outer surfaces of the cork stoppers with a film having a morphologically reticulated structure having cells smaller in size than the cork cells of the cork stoppers so as to act as a barrier against dust and impurities penetrating the cork stoppers and simultaneously allowing the passage of oxygen.

2. The method according to claim 1, wherein the film comprises a nanostructured coating structure having a nanometric cell size in the order $10^{-9}$.

3. The method according to claim 2, wherein the film is selected from the group consisting of carbon, carbon derivatives, and other amorphous carbon structures.

4. The method according to claim 2, comprising an initial operation of surface sanification and purification of the cork stoppers including:
  a) a material cleaning step carried out within a vacuum apparatus maintained at $10^{-2}$ to $10^{-8}$ bar, and a maximum temperature of 60° C.,
  whereby gases are released from the cork mass of the cork stoppers;
  b) a washing step carried out by introducing into the vacuum apparatus maintained at $10^{-2}$ to $10^{-8}$ bar, gases selected from the group consisting of hydrogen, helium, nitrogen, argon, and mixtures thereof, thereby eliminating and/or inhibiting organic material inside and on the surface of the cork stoppers; followed by the second operation of coating the surfaces of the cork cells of the cork stoppers and the outer surfaces of the cork stoppers with the nanostructured film.

* * * * *